| United States Patent [19] | [11] 3,932,514 |
|---|---|
| Thelen et al. | [45] Jan. 13, 1976 |

[54] CATALYST FOR THE PREPARATION OF CYCLOHEXANONE FROM PHENOL AND PROCESS THEREFOR

[75] Inventors: Hermann Thelen, Krefeld-Bockum; Kurt Halcour, Leverkusen; Wulf Schwerdtel, Cologne; Wolfgang Swodenk, Odenthal-Globusch, all of Germany

[73] Assignee: Bayer Aktiengesellschaft, Leverkusen, Germany

[22] Filed: Feb. 23, 1973

[21] Appl. No.: 335,216

Related U.S. Application Data

[62] Division of Ser. No. 180,150, Sept. 13, 1971, abandoned.

[30] Foreign Application Priority Data

Sept. 17, 1970 Germany............................ 2045882

[52] U.S. Cl........................ 260/586 P; 252/466 PT

[51] Int. Cl.² ........................................ C07C 45/00
[58] Field of Search................... 260/586 R, 586 P; 252/466 A, 466 PT

[56] References Cited
UNITED STATES PATENTS

| 2,087,691 | 7/1937 | Lazier ......................... 260/586 R X |
|---|---|---|
| 2,328,719 | 9/1940 | Houghton et al. .......... 260/586 R X |
| 2,588,359 | 3/1952 | Chitwood et al............ 260/586 R X |
| 3,373,219 | 3/1968 | Kronig et al. .................... 252/466 A |
| 3,459,657 | 8/1969 | Kronig et al. .................... 252/466 A |
| 3,600,429 | 8/1971 | Kronig et al. .................... 252/466 A |

*Primary Examiner*—Norman Morgenstern
*Attorney, Agent, or Firm*—Burgess, Dinklage & Sprung

[57] ABSTRACT

A palladium catalyst on an aluminum spinel carrier is used to selectively hydrogenate phenol to cyclohexanone.

9 Claims, No Drawings

CATALYST FOR THE PREPARATION OF CYCLOHEXANONE FROM PHENOL AND PROCESS THEREFOR

RELATED APPLICATION

This application is a division of co-pending application Ser. No. 180,150 filed Sept. 13, 1971 and now abandoned.

BACKGROUND

This invention relates to a highly active palladium catalyst, in which spinels are used as carrier material, for the preparation of cyclohexanone by selective vapour phase hydrogenation of phenol and to the process for using the said catalyst.

In U.S. Pat. No. 3.305.586 it has been disclosed that phenol can be hydrogenated to cyclohexanone by means of a catalyst of palladium on alumina as carrier. The process provides either high conversion rates with low selectivity or high selectivity with low conversion rates. The degree of purity in which the cyclohexanone is obtained from the hydrogenation process is of great economic importance for the working up of the hydrogenation product in order to obtain pure cyclohexanone.

According to U.S. Pat. No. 3.076.810 which describes a process for the preparation of cyclohexanone from phenol, an improvement in yield is obtained if the alumina used as carrier material is impregnated with 0.1 to 1% by weight of sodium in the form of sodium carbonate or sodium hydroxide. In order to obtain sufficiently high selectivity at these high conversion rates, however, the hydrogenation of phenol over this catalyst requires residence times of from 2½ to 5 hours, which are too long to be of technical interest. British Patent Specification No. 1.063.357 describes a process for the preparation of cyclohexanone by vapour phase hydrogenation of phenol in which the catalyst carrier used is a mixture of 40 to 98% by weight of γ-alumina and 2 to 60% by weight of alkaline earth metal hydroxide. However, the conversion rates of phenol are low when hydrogenation of phenol is carried out using this palladium-containing carrier.

According to DDR Patent Specification No. 69 585, higher conversion rates and selectivity are achieved if the alumina (40 to 98% by weight) is mixed with a mixture of alkaline earth metal hydroxides (2 to 60% by weight), the alumina used containing either α-alumina or χ-alumina addition to γ-alumina.

The catalyst carrier is itself prepared by adding graphite to a mixture of alumina and alkaline earth metal hydroxides and pressing the resulting mixture to form cylindrical carriers. A serious disadvantage of catalyst carriers prepared in this way is that their mechanical hardness is generally low.

SUMMARY

It has been found that hard and highly active catalysts with long lasting activity are obtained by using, as catalyst carrier, alumina which has been completely or partly converted into spinel. Such spinels are obtained by reacting alumina with compounds of monovalent or divalent metals such as lithium, magnesium, cobalt, manganese or zinc (see Gmelin, System No. 35, A1, I1, Al,Tl, A, 1934 - 1935 pages 26 - 28 and Ullmanns Encyklopaedie der technischen Chemie 3rd Edition (1955) Volume 6, pages 242 - 244). By using alumina in the form of balls as starting material for the production of spinels, the carriers obtained are not only distinguished by their high mechanical strength but they also have optimum properties by virtue of their spherical form, e.g. for use as catalyst carriers in a fixed bed reactor. In addition, the conversion into the spinel form substantially increases the selectivity and yield of the carriers as compared with pure alumina used as carrier for palladium in the gas phase hydrogenation of phenol to cyclohexanone.

DESCRIPTION

It was to be expected from the known state of the art that the preparation of cyclohexanone by selective gas phase hydrogenation of phenol on palladium catalysts could be achieved with high selectivity, high yields and long catalyst life only if a carrier material which is basic in reaction was used. It must therefore be regarded as distinctly suprising that the same effect can also be achieved with carrier material consisting of spinel types which are not alkaline in reaction. Another advantage of the process of the present invention is that the spinels used as carrier material are distinguished by great hardness and that moreover the catalyst used according to the invention can be produced by a very simple method.

The amount of spinel formation should be at least 20%. Carriers in which the alumina is present practically completely in the form of spinel have been found to be very suitable. It is advantageous to prepare the spinel form from highly active alumina in the form of lumps having an internal surface area of 200 to 350 $m^2/g$. All forms of alumina which are still absorbent and which form spinels when annealed in the presence of spinel-forming metal salts may be used for this purpose. The pieces of alumina, for example in the form of extrudes, pellets, pills or, preferably balls measuring 2 to 10 mm may be impregnated with the solution of a compound (salt, hydroxide) of the spinel forming metal which is to be used, and dried. If salts have been used for impregnating the particles, they should be converted into their hydroxides and then heated to 250°C to 650°C, if desired with the addition of gases which contain oxygen or water vapour, to convert them into the oxides. Alternatively, salts which can be directly converted into their oxides by heat may be used (e.g. nitrates and salts of organic acids). Spinel formation is then brought about by heating to 900°C to 1300°C, e.g. for 1 to 6 hours. Stoichiometric spinel formation may be achieved if desired by carrying out the impregnation with the given solution after a drying operation and, if necessary, repeating the process of decomposing the salts several times. If desired, mixed spinels may be prepared by using several spinel forming metal compounds. According to the invention, the metals used for spinel formation are preferably the following: cobalt, magnesium, lithium, nickel or zinc. The time of the annealing process and the annealing temperature vary with the different spinels. The annealing temperature and annealing time have an influence on the internal surface area and pore diameter of the carrier. Average pore diameters of catalyst carrier of from 200 to 800 A and internal surface areas of from 20 to 120 $m^2/g$ have been found to be suitable.

The advantage of the catalyst carrier according to the invention is that it can be prepared from a hard alumina which is already shaped and which has even greater hardness and abrasion resistance after spinel formation and annealing.

The palladium may be applied to the carrier in known manner in quantities of e.g. 0.1 to 10% by weight, preferably 0.5 to 5% by weight, by impregnating the carrier e.g. with an aqueous solution of a palladium salt. In principle, any commercially available palladium compound may be used for this impregnation. Reduction of the salt (preferably the chloride) to the metal, which normally follows impregnation, may be carried out e.g. with formaldehyde in alkaline solution but any other reducing methods may also be used.

The catalysts prepared as described above are suitable for the selective vapour phase hydrogenation of phenol to cyclohexanone under conditions known per se, and long operational runs, high yields and high selectivity are achieved.

EXAMPLES a. Preparation of the catalysts:

Catalyst 1

2.86 Litres of γ-alumina balls having a diameter of a 4 to 6 mm and an internal surface area of about 250 m²/g were impregnated with 1 liter of an aqueous solution at 30°C, into which solution 296 g of formic acid and 233 g of 54% aqueous lithium hydroxide solution had been introduced. The saturated alumina was dried under vacuum at 150°C, again impregnated with the same solution and again dried under vacuum at 150°C. The carrier was then annealed at 1050°C for 6 hours, thus being converted into a spinel, as could be determined by X-ray investigation. The finished carrier had an internal surface area of 25 m²/g and an average pore size of 700 A. After impregnation with a hydrochloric acid solution of 82.7 g of palladium-(II) chloride hydrate and reduction with alkaline formalin, the finished catalyst contained 1.8% by weight of palladium. More than 99% of the balls had a minimum rupture strength of 10.0 kg/ball.

Catalyst 2

1.2 Liters of active alumina in the form of balls having a diameter of 4 mm and an internal surface area of 288 m²/g were impregnated three times at room temperature with 1.600 g of a saturated aqueous solution of cobalt -(II) nitrate. The cobalt nitrate was converted to the oxide by heating the impregnated and dried balls to 500°C. The oxide was then heated to 1050°C for 8 hours. This brought about conversion into the spinel form, as could be demonstrated by X-ray investigation of the structure. The carrier obtained in this way had an internal surface area of 40 m²/g and an average pore size of 760 A. The catalyst was prepared by impregnating the carrier with 50 g of palladium-(II) chloride hydrate in hydrochloric acid solution. The palladium was reduced with alkaline formalin. The palladium content of finished catalyst was 1.8% by weight. 99% of finished catalyst had a minimum rupture strength of 8.9 kg/ball.

Catalyst 3

The catalyst was prepared by the same method as described for catalyst 2 but 1800 g of a saturated aqueous solution of magnesium nitrate was used instead of a solution of cobalt nitrate. The quantity of magnesium nitrate used corresponded to a spinel formation of 60% according to X-ray investigation of the structure. The carrier was impregnated with 50 g of palladium-(II) chloride hydrate in hydrochloric acid solution so that after the reduction carried out as in Example 1 the finished catalyst contained 1.8% by weight of palladium, and 99% of the balls had a minimum rupture strength of 8.8 kg/ball.

Catalyst 4

The catalyst carrier was prepared from 1.2 l of γ-alumina in the form of extrudes measuring 4 to 6 mm and having an internal surface area of 300 m²/g. 1600 g of a saturated solution of zinc nitrate were added several times to the alumina extrudes. A zinc-aluminum spinel which had a stoichiometric composition was formed. The impregnated carrier was dried and heated to 500°C to decompose the nitrate into the oxide. The carrier was then heated to 1050°C for 6 hours. The resulting carrier consisted of zinc-alumina spinel according to X-ray investigation of its structure. It had an internal surface area of 20 m²/g and an average pore size of 800 A. After impregnation with 55 g of palladium–chloride hydrate in hydrochloric acid solution, 2 hours reduction in a stream of hydrogen at 200°C and washing free from chloride, the catalyst contained 1.8% by weight of palladium. At least 99% of the extrudes of the finished catalyst had a minimum rupture strength of 8.3 kg/particle.

Catalyst 5 (Comparison control 1, alumina without additives)

36 g of palladium-(II) chloride hydrate in hydrochloric acid solution were applied to 1000 g of γ-alumina balls which had a particle diameter of 4 to 6 mm and an internal surface area of 280 m²/g. After reduction with aqueous alkaline formalin, the catalyst contained 1.8% by weight of palladium. At least 95% of the balls had a maximum rupture strength of only 2.6 kg/ball.

Catalyst 6 (Comparison control 2, alumina without additives)

36 g of palladium-(II) chloride hydrate in hydrochloric acid solution were applied to 1000 g of an α-alumina which was in the form of extruded pieces having a diameter and length of about 5 mm and an internal surface area of 30 m²/g, the addition of palladium chloride hydrate being interrupted three times by periods of drying of the alumina. After reduction with aqueous formalin, the catalyst contained 1.8% by weight of palladium. 95% of the extrudes had a maximum rupture strength of only 4.5 kg/particle.

b. Hydrogenation:

Example 1 (this invention)

2000 ml of catalyst 1 described above were introduced into a reaction furnace which had an internal width of 50 mm and a length of 1 mm and which was provided with an oil filled heating or cooling jacket. After the catalyst had been treated with hydrogen at 200°C for about 24 hours, 660 g of phenol vapour and 990 liters of hydrogen were passed over the catalyst, the heat of reaction being removed by the oil in the cooling jacket. Catalyst temperatures between 150°C and 220°C were established, a clear temperature peak being observed. The ratio of phenol: hydrogen is 1 mol:6 mol. The reaction product obtained contains on an average 93% of cyclohexanone, 6% of cyclohexanol and about 1% of impurities, the phenol content being less than 0.1%, i.e. conversion may be regarded as 100%.

The reaction product is purified by vacuum distillation and yields a cyclohexanone of exceptional purity, as can be determined by gas chromatographic analysis. After a reaction time of 2500 hours, the selectivity drops to below 90% of cyclohexanone and the conversion also drops. In this experiment, 1 litre of catalyst produced 830 kg of cyclohexanone. Similar results are achieved with catalysts 2 to 4.

Example 2 (comparison example)

When the catalysts 5 and 6 are subjected to the conditions described in example 1 above, the selectivity and conversion drop after 190 hours and 130 hours, respectively. In this experiment, 1 liter of catalyst produces 58 kg of cyclohexanone.

It is clear that the catalyst carrier according to the invention (lithium-aluminum spinel) has distinct advantages over a catalyst based on alumina.

We claim:

1. In a process for the preparation of cyclohexanone by the selective hydrogenation of phenol in the vapor phase, the improvement which comprises carrying out the hydrogenation in the presence of a palladium catalyst on an aluminum spinel carrier obtained by annealing alumina with compounds of monovalent or divalent spinel forming metals followed by impregnation of the thus formed spinel carrier with a palladium salt which is subsequently reduced to the metal, said catalyst containing 0.1 to 10% by weight palladium.

2. Process of claim 1, carried out at 100°C to 350°C.

3. Process of claim 1, carried out at normal, reduced or elevated pressure.

4. Process of claim 1 wherein said spinel forming metals are selected from the group of lithium, magnesium, nickel, cobalt, mangenese and zinc.

5. Process of claim 1 wherein the amount of spinel formation in said carrier is at least 20%.

6. Process of claim 1 wherein said spinel carrier is formed from highly active alumina in the form of lumps having an internal surface area of 200–350 m²/g.

7. Process of claim 1 wherein said spinel carrier has average 4 diameters of from 200–800 A.

8. Process of claim 1 wherein said spinel carrier has an internal surface area of from 20–120 m²/g.

9. Process of claim 1 wherein the amount of palladium on said carrier is in the range of 0.1–10 percent by weight.

* * * * *